US010080675B2

(12) United States Patent
Fox et al.

(10) Patent No.: US 10,080,675 B2
(45) Date of Patent: Sep. 25, 2018

(54) SYSTEM AND METHOD FOR CONDITIONING AN ENDOPROSTHESIS

(71) Applicant: Abbott Cardiovascular Systems Inc., Santa Clara, CA (US)

(72) Inventors: Julia C. Fox, San Carlos, CA (US); Leah Compas, Palo Alto, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 281 days.

(21) Appl. No.: 14/833,795

(22) Filed: Aug. 24, 2015

(65) Prior Publication Data
US 2017/0056218 A1    Mar. 2, 2017

(51) Int. Cl.
   *A61F 2/97*     (2013.01)
   *A61F 2/966*    (2013.01)
   *A61F 2/915*    (2013.01)

(52) U.S. Cl.
   CPC ............... *A61F 2/97* (2013.01); *A61F 2/966* (2013.01); *A61F 2/915* (2013.01); *A61F 2002/91533* (2013.01); *A61F 2002/91575* (2013.01); *A61F 2210/0004* (2013.01); *A61F 2240/001* (2013.01)

(58) Field of Classification Search
   CPC ........ A61F 2/95; A61F 2/97; A61F 2240/001; B29C 71/00; B29C 53/083
   See application file for complete search history.

(56) References Cited

U.S. PATENT DOCUMENTS

| 7,476,245 | B2 | 1/2009 | Abbate |
| 8,002,817 | B2 | 8/2011 | Limon |
| 8,414,528 | B2 | 4/2013 | Liu et al. |
| 2002/0035391 | A1 | 3/2002 | Mikus et al. |
| 2006/0030923 | A1 | 2/2006 | Gunderson |
| 2011/0224778 | A1 | 9/2011 | Gale |
| 2013/0166020 | A1* | 6/2013 | Hillukka ............... A61F 2/2427 623/2.11 |
| 2014/0157567 | A1* | 6/2014 | Wang .................... A61F 2/0095 29/428 |
| 2014/0379064 | A1 | 12/2014 | Pacetti et al. |
| 2017/0000634 | A1* | 1/2017 | Helmick ................. A61F 2/958 |

OTHER PUBLICATIONS

ASTM International, ASTM F2394-07 "Standard Guide for Measuring Securement of Balloon Expandable Vascular Stent Mounted on Delivery System," Aug. 2007.
British Standards Institution, BS EN ISO 25539-2:2012 "Cardiovascular Implants—Endovascular devices—Part 2: Vascular Stents," Jan. 31, 2013.

* cited by examiner

*Primary Examiner* — Thomas McEvoy
(74) *Attorney, Agent, or Firm* — Squire Patton Boggs (US) LLP

(57) ABSTRACT

An endoprosthesis is conditioned prior to use within a patient by placing a scaffold of the endoprosthesis in contact with a sterile liquid optionally at body temperature, following by causing the scaffold to bend. The scaffold may be bent by moving the scaffold through a conditioning tube.

11 Claims, 12 Drawing Sheets

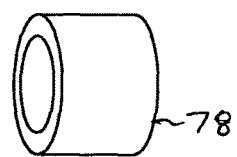
FIG. 15
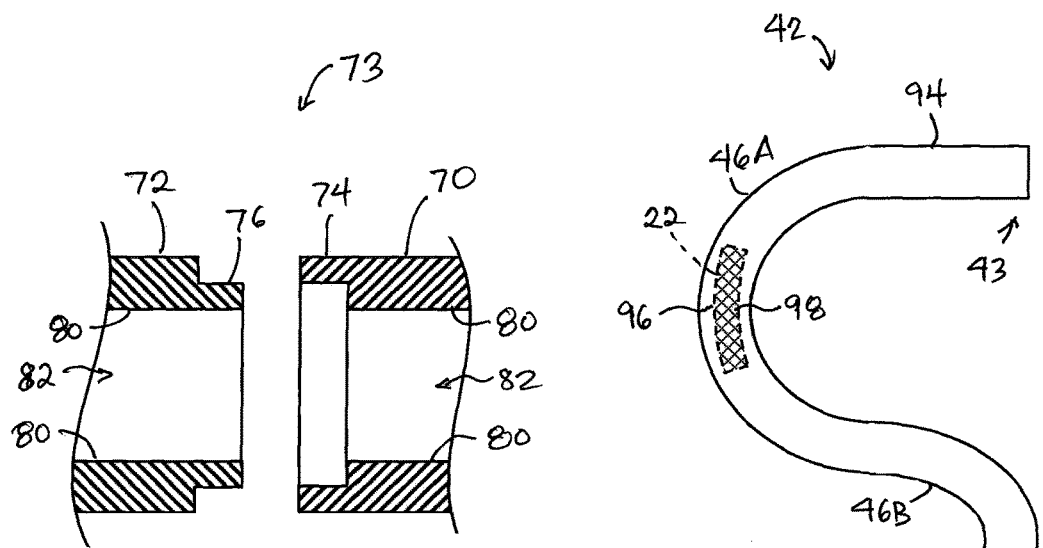
FIG. 16
FIG. 17

SYSTEM AND METHOD FOR CONDITIONING AN ENDOPROSTHESIS

FIELD

The invention relates, in general, to medical devices and, more particularly, a system and method for preparing an endoprosthesis prior to use.

BACKGROUND

An endoprosthesis is an artificial device that is placed inside the body, usually within an anatomical lumen. An anatomical lumen is a cavity within the body, typically a tubular organ. Examples of anatomical lumen include without limitation a urinary tract, bile duct, fallopian tube, esophagus, and arterial or venous vasculature. Stents are a type of endoprosthesis which are often used in the treatment of atherosclerotic stenosis in blood vessels. Stenosis refers to a narrowing or constriction of the diameter of an anatomical lumen or orifice. Stents can reinforce the walls of the anatomical lumen and prevent a reoccurrence of stenosis.

Stents may include a scaffold of interconnected structural members, which are referred to as stent struts. Scaffolds were typically made of shape memory metal, such as nickel-titanium alloy, due to demanding design requirements. Requirements include having to be very small (sometimes just a few millimeters in diameter) and having to withstand conditions within a human or animal body for long periods of time. Also, scaffolds are often collapsed or crimped before introduction into to the patient. When in a crimped state, the scaffold may be delivered through tight and tortuous anatomical lumen. When at the intended implantation site, the scaffold is allowed to self-expand or is forcibly expanded.

Scaffolds are often crimped onto catheters which are used to deliver the scaffold to the intended implantation site. A scaffold is required to remain attached to the catheter when traveling through the patient, during which time the scaffold may be exposed to bodily fluids and subjected to significant friction from the walls of anatomical lumen at constrictions and sharp bends. The ability of the scaffold to remain attached to a catheter can be measured according to industry guidelines, such as ASTM F2394-07. In ASTM F2394-07, a securement test performed by a device manufacturer measures the ability of the scaffold remain attached to a catheter balloon. However, a securement test on a freshly crimped scaffold may provide unrealistically favorable results. To avoid this, a pre-test treatment may be performed by the device manufacturer prior to the securement test. The pre-test treatment simulates conditions to which the scaffold might be exposed prior to and/or during clinical use. The pre-test treatment may simulate shipping and handling conditions, pre-soaking, and conditions in anatomical lumen.

Advancements in scaffold design have led to the use of polymers for the core material of the scaffold. Scaffolds made of bioresorbable polymers are designed to degrade after a period of time in order provide certain advantages over metal scaffolds. However, polymer scaffolds usually must satisfy the same basic requirements mentioned above for metal scaffolds. Satisfying those requirements can be challenging since polymers are often not as strong as metals. Generally, a polymer stent strut must be thicker to achieve the same mechanical strength as a metal strut, but there are limits to how much struts may be thickened due to size constraints imposed by anatomical lumen. Also, thicker polymer struts may reduce flexibility of the scaffold, which may make it more difficult to deliver the scaffold through constrictions and sharp bends of anatomical lumen.

Deliverability of the scaffold through constrictions and sharp bends may be enhanced via appropriate design of stent strut patterns, careful selection of polymer materials, and/or special processing designed to increase inherent material strength. Still, there is a continuing need to enhance deliverability of polymer scaffolds through tight and tortuous anatomical lumen.

SUMMARY

Briefly and in general terms, the present invention is directed to a system and method for conditioning an endoprosthesis and to a method of using an endoprosthesis.

In aspects of the present invention, a method for conditioning comprises opening a sterilized package containing the endoprosthesis, the endoprosthesis including a scaffold having a substrate formed of a bioresorbable polymer material. Said opening is followed by placing the scaffold in contact with a sterile liquid. Said placing is followed by causing the scaffold to bend along a longitudinal axis of the scaffold before the endoprosthesis is used within a patient.

In aspects of the present invention, a system comprises a catheter, an endoprosthesis, and a conditioning tube. Said catheter includes a proximal segment and a distal segment. Said endoprosthesis is disposed on the distal segment of the catheter. The endoprosthesis includes a scaffold having a substrate formed of a bioresorbable polymer material. The scaffold includes an outer surface and an inner surface. The outer surface defines an outer diameter. The inner surface defines a lumen having a longitudinal axis extending centrally through the lumen. Said conditioning tube is disposed outside of a human or animal body. The conditioning tube includes a passageway configured to receive the catheter and the endoprosthesis. The passageway includes at least one turn. Each turn has an inner surface defining a curvature radius, an inner diameter, and an arc degree. The curvature radius, the inner diameter, and arc degree are sized such that the scaffold must bend along the longitudinal axis of the scaffold in order for the catheter and endoprosthesis to move entirely through the turn.

A method of using an endoprosthesis comprises conditioning the endoprosthesis, followed by introducing the endoprosthesis into a human or animal body.

The features and advantages of the invention will be more readily understood from the following detailed description which should be read in conjunction with the accompanying drawings.

BRIEF DESCRIPTION OF THE DRAWINGS

FIG. 15 is a perspective view of an exemplary coupler for use at the coupling region in FIG. 13.

FIG. 16 is a cross-section view showing an exemplary configuration for the coupling region in FIG. 13.

FIG. 17 is a schematic view of an exemplary conditioning tube used for flexing a scaffold.

DETAILED DESCRIPTION OF EXEMPLARY EMBODIMENTS

As used herein, "bioresorbable" refers to a material capable being completely eroded, degraded (either biodegraded and/or chemically degraded), and/or absorbed when exposed to bodily fluids (such as blood or other fluid); and can be gradually resorbed, absorbed and/or eliminated by the body. Other terms such as biodegradable, bioabsorbable, and bioerodible may be found in the literature and while these terms have specific definitions, they are often used interchangeably.

Figure 1:
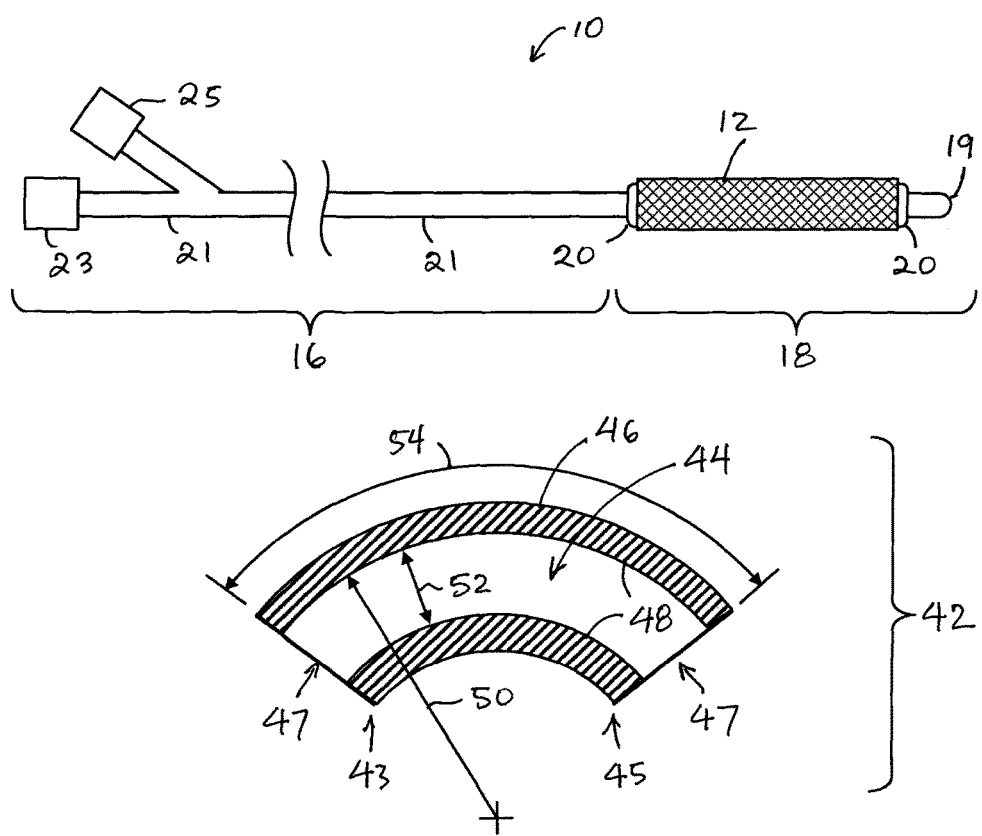
FIG. 1 is a schematic view of an exemplary system for conditioning an endoprosthesis.

Referring now in more detail to the exemplary drawings for purposes of illustrating aspects of the invention, wherein like reference numerals designate corresponding or like elements among the several views, there is shown in FIG. 1 exemplary system 10 for conditioning an endoprosthesis prior to use within a patient. System 10 includes endoprosthesis 12 mounted on catheter 14. Endoprosthesis 12 can be a stent, graft tube, stent-graft, shunt, or other medical device configured for implantation in the body of a patient. Catheter 14 includes proximal segment 16 and distal segment 18.

Proximal segment 16 is directly attached to distal segment 18. Distal segment 18 includes catheter tip 19 and inflatable balloon 20 on which endoprosthesis 12 has been mounted, such as by crimping or other method. Proximal segment 16 includes flexible catheter body 21 connected to catheter hub 23 and connector 25. Hub 23 may include controls to steer catheter 14 when the catheter is in the patient. Hub 23 may also include an aperture to receive a guidewire for guiding distal end 18, including balloon 20 and endoprosthesis 12, to a desired location within the patient. Connector 25 includes an aperture for injecting fluid into catheter 14 for inflating balloon 20 when at the desired location within the patient.

Catheter 14 may vary from what is illustrated herein. For example, the catheter need not have a balloon, hub, or connector. Endoprosthesis 12 may be mounted directly onto the catheter body instead of a balloon. The type of catheter may depend on the type of endoprosthesis it is intended to carry and other factors.

Figure 2:
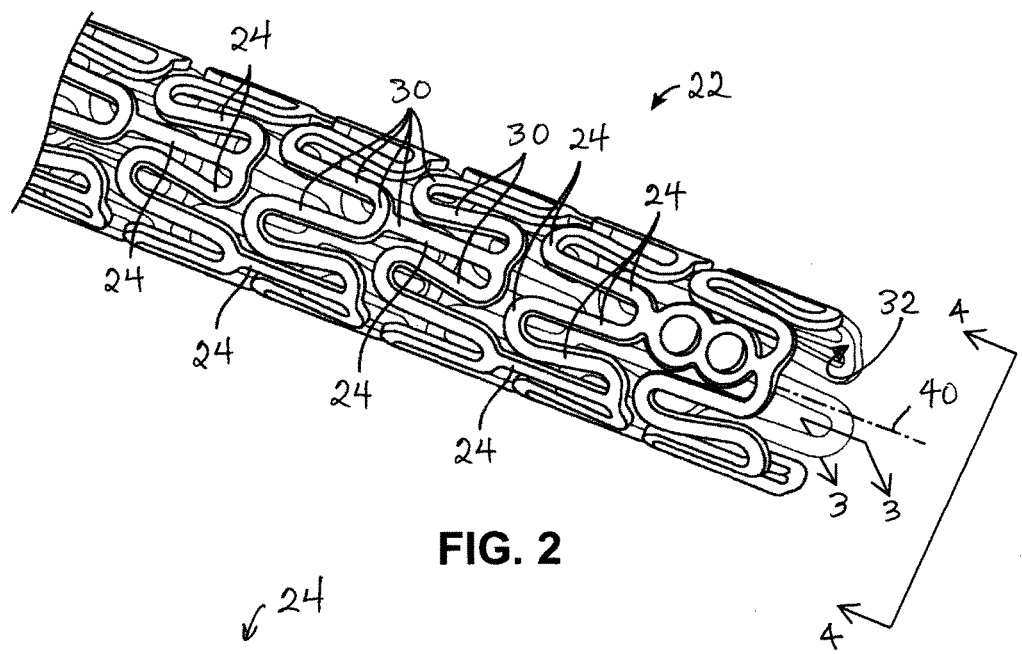
FIG. 2 is a perspective view of an exemplary scaffold of an endoprosthesis.

Referring to FIG. 2, endoprosthesis 12 includes scaffold 22 formed by interconnected struts 24. That is, endoprosthesis 12 may consists of scaffold 22 alone or may be comprised of scaffold 22 and another structure. Only scaffold 22 is illustrated in FIG. 2 to more clearly show struts 24. It is to be understood that endoprosthesis 12 (FIG. 1) may include other structures, such as a graft tube or other device, in addition to scaffold 22.

The arrangement of struts 24 may vary from what is illustrated herein. The arrangement of struts 24 may vary depending, for example, on the type of endoprosthesis to which scaffold 22 belongs. For example, the arrangement of struts suitable for use with a graft may vary from an arrangement suitable for a solitary stent. The arrangement of struts may also vary depending on the intended implantation location. For example, the arrangement of struts suitable for a blood vessel may vary from an arrangement intended for the urinary tract, fallopian tube, Eustachian tube, or other anatomical lumen. The arrangement of struts 24 may be as described in U.S. Pat. Nos. 7,476,245 and 8,002,817 and U.S. Application Publication No. 2011/0224778, which are incorporated herein by reference.

Figure 3:
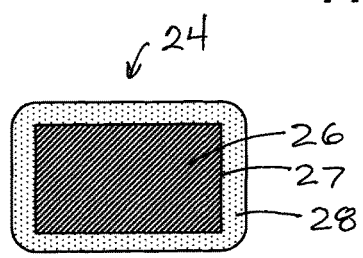
FIG. 3 is a cross-section view of an exemplary strut taken along line 3-3 in FIG. 2.

As shown in FIG. 3, scaffold 22 has substrate 26 formed of a bioresorbable polymer material. Substrate 26 is the structural core of struts 24. Substrate 26 provides scaffold 22 with the mechanical strength required to perform its intended function, such as to prevent restenosis of an anatomical lumen or to support a graft or other device. Scaffold may include coating 28 applied onto substrate 26, such as by spraying, dip coating, or other process known in the art. Coating 28 is formed of a polymer material, which can be the same as or different from the bioresorbable polymer material of substrate 26. The polymer material of coating 28 may carry a drug or other therapeutic agent. For example, coating 28 may include everolimus, sirolimus, and/or derivatives thereof. Even with the presence of coating 28, most of the mechanical strength of scaffold 22 is provided by substrate 26.

Figure 4:
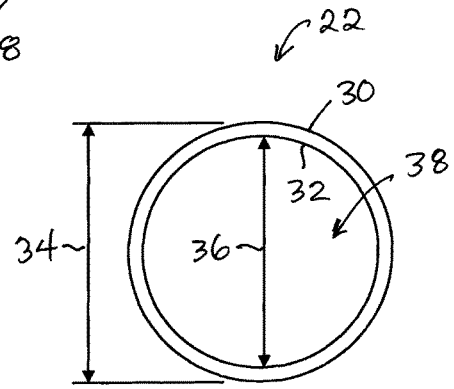
FIG. 4 is an end view of the scaffold taken along line 4-4 in FIG. 2.

As shown in FIG. 4, scaffold 22 is tubular and includes outer surface 30 and inner surface 32. The radially outward facing surfaces of struts 24 (FIG. 2) collectively form outer surface 30. The radially inward facing surfaces of struts 24 collectively form inner surface 32. Outer surface 30 defines outer diameter 34 of scaffold 22. Inner surface 32 defines inner diameter 36 of scaffold 22. Inner surface 32 also defines lumen 38, which is the central channel within scaffold 22. Lumen 38 has longitudinal axis 40 (FIG. 2) that extends through the center of lumen 38.

Referring again to FIG. 1, system 10 further includes a sterile conditioning tube 42. Catheter 14 and endoprosthesis 12 are intended for use within the patient, whereas conditioning tube 42 is used only outside the patient. Preferably, conditioning tube 42 has been sterilized to the same level of sterility as catheter 14 and endoprosthesis 12 since catheter 14 and endoprosthesis 12 will come into contact with conditioning tube 42 prior to introduction of catheter 14 and endoprosthesis 12 within a human or animal patient.

Conditioning tube 42 is a device that can apply a controlled amount of flexing to scaffold 22 before scaffold 22 is introduced in the patient. Conditioning tube 42 has two ends 43 and 45. Aperture 47 is present at both ends 43 and 45. Alternatively, one of the ends may be closed.

In use, scaffold 22 is forced through conditioning tube 42, which causes scaffold 22 to bend. The user may force scaffold 22 through conditioning tube 42 one or more times, as appropriate. Without intending to be being bound by theory, it is believed that causing scaffold 22 to bend slightly prior to use within a patient may increase flexibility of struts 24 and/or other structures of endoprosthesis 12. Increased flexibility via mechanical flexing may facilitate subsequent insertion of endoprosthesis 12 through narrow and tortuous anatomical lumen of the patient.

As shown in FIG. 1, conditioning tube 42 includes passageway 44 configured to receive catheter 14 and endoprosthesis 12. Scaffold 22 is forced through conditioning tube 42 by inserting distal segment 18 of catheter 14 into aperture 47 and passageway 44. Passageway 44 includes turn 46 having inner surface 48. A "turn" is defined as segment of passageway 44 that is not straight. Inner surface 48 defines curvature radius 50, inner diameter 52, and arc degree 54. The term "curvature radius" is the same as "radius of curvature" known in the art. Also, the term "arc degree" is the same as "degree of arc" known in the art. Curvature radius 50 is measured from a point outside of passageway 44 to an outermost portion or point of inner surface 48 of turn 46. Curvature radius 50, inner diameter 52, and arc degree 54 are sized such that scaffold 22 must bend along longitudinal axis 40 (FIG. 1) of the scaffold in order for catheter 14 and endoprosthesis 12 to travel completely through turn 46.

In FIG. 1, turn 46 forms the entire conditioning tube 42. Alternatively, the conditioning tube optionally includes straight segments. Also, the conditioning tube optionally includes two or more connected turns extending in different directions.

Figure 5:
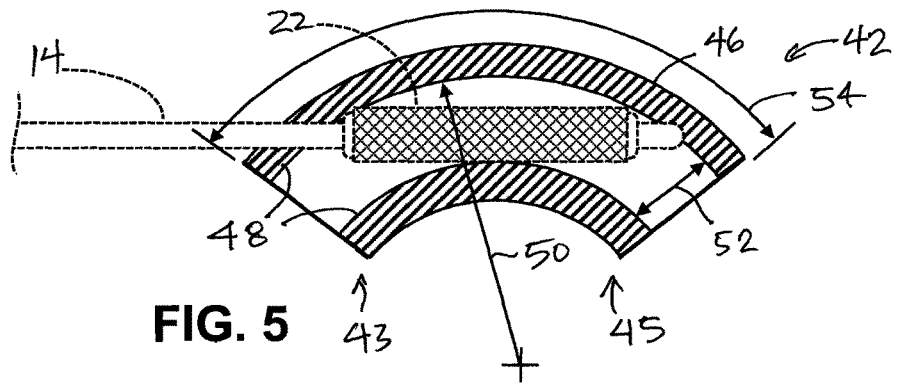
FIG. 5 is a cross-section view of the conditioning tube of FIG. 1 with a superimposed image of a catheter and endoprosthesis in a straight state.

FIG. 5 illustrates an example where curvature radius 50, inner diameter 52, and arc degree 54 are sized such that scaffold 22 must bend along longitudinal axis 40 of scaffold 22 in order for catheter 14 and endoprosthesis 12 to move through turn 46. Curvature radius 50, inner diameter 52, and arc degree 54 are the same as in FIG. 4. Arc degree 54 is about 95 degrees. In FIG. 5, an illustration of catheter 14 and endoprosthesis 12 while in a straight state is superimposed over an illustration of turn 46 of conditioning tube 42. It can be seen that inner surface 48 of turn 46 would not allow scaffold 22 to travel through turn 46 while scaffold 22 is in a straight state.

Conditioning tube 42 is configured to maintain its shape when catheter 14 and endoprosthesis 12 are forced through turn 46. Curvature radius 50, inner diameter 52, and arc degree 54 remain the same when catheter 14 and endoprosthesis 12 are forced through turn 46.

Figure 6A:
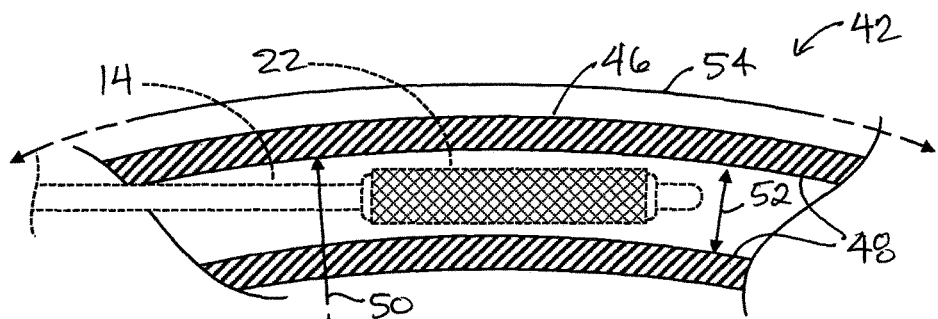
FIGS. 6A and 6B are cross-section views of different conditioning tubes in which one or more design parameters have been altered from the conditioning tube of FIG. 5.
Figure 7A:
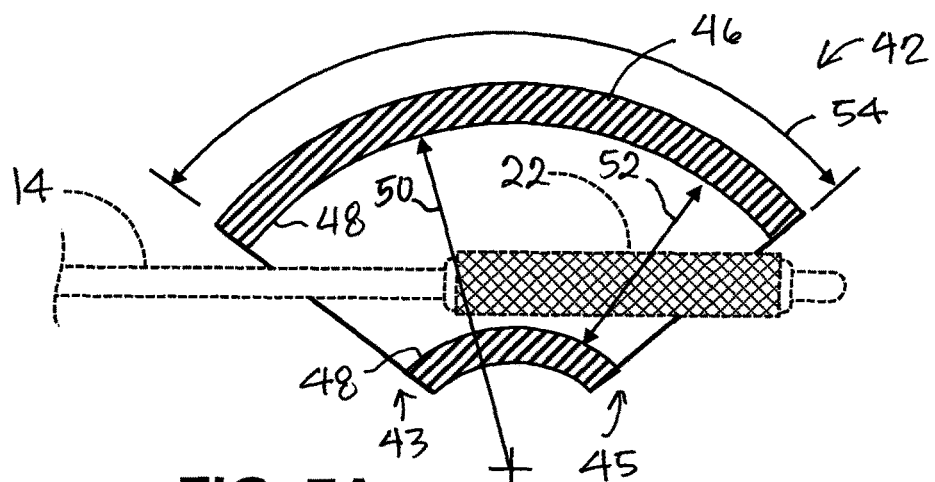
FIGS. 7A and 7B are cross-section views of different conditioning tubes in which one or more design parameters have been altered from the conditioning tube of FIG. 5.

FIGS. 6A and 7A illustrate examples in which curvature radius 50, inner diameter 52, and arc degree 54 are not sized such that scaffold 22 must bend along its longitudinal axis in order for catheter 14 and endoprosthesis 12 to move through turn 46.

In FIG. 6A, curvature radius 50 is too large in relation to inner diameter 52 and arc degree 54. Although inner diameter 52 and arc degree 54 are the same as in FIG. 5, it can be seen that inner surface 48 of turn 46 would allow scaffold 22 to remain straight while traveling through turn 46. As previously mentioned, the arc degree of turn 46 in FIG. 5 is about 95 degrees. In FIG. 6A, only a portion of turn 46 is shown and it is to be understood that turn 46 continues beyond the page to form a 95 degree arc. In FIG. 6A, the body of catheter 14 will bend slightly when travelling through turn 46, but the slight bend of the catheter body does not force scaffold 22 to bend.

Figure 6B:
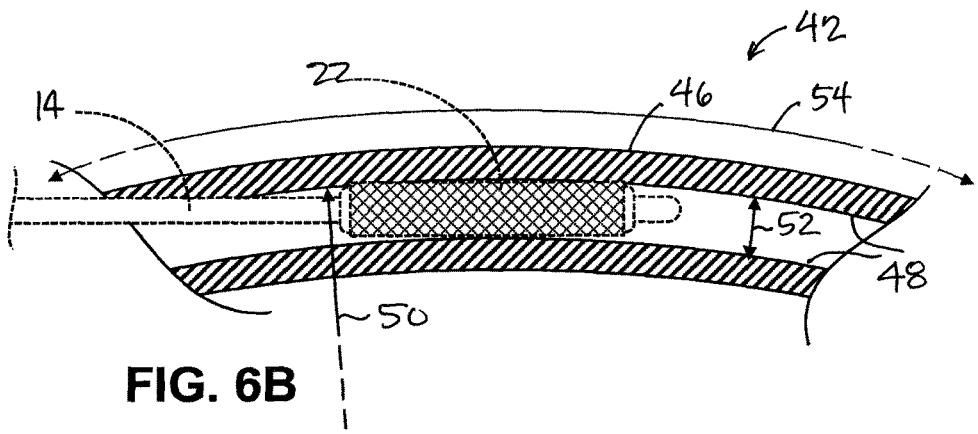

If inner diameter 52 in FIG. 6A were modified to be smaller as shown in FIG. 6B, then inner surface 48 of turn 46 would force scaffold 22 to bend while traveling through turn 46. In FIG. 6B, curvature radius 50 and arc degree 54 (both of which are the same as in FIG. 6A) and inner diameter 52 (which is smaller than in FIG. 6A) are sized such that scaffold 22 must bend along its longitudinal axis in order for catheter 14 and endoprosthesis 12 to travel completely through turn 46.

In FIG. 7A, inner diameter 52 is too large in relation to curvature radius 50 and arc degree 54. Although curvature radius 50 and arc degree 54 are the same as in FIG. 5, it can be seen that inner surface 48 of turn 46 would allow scaffold 22 to remain straight while traveling through turn 46. In FIG. 7A, scaffold 22 is not forced to bend since the body of catheter 14 and scaffold 22 are able to pass through the entire 95 degree arc of turn 46 without making contact with inner surface 48.

Figure 7B:
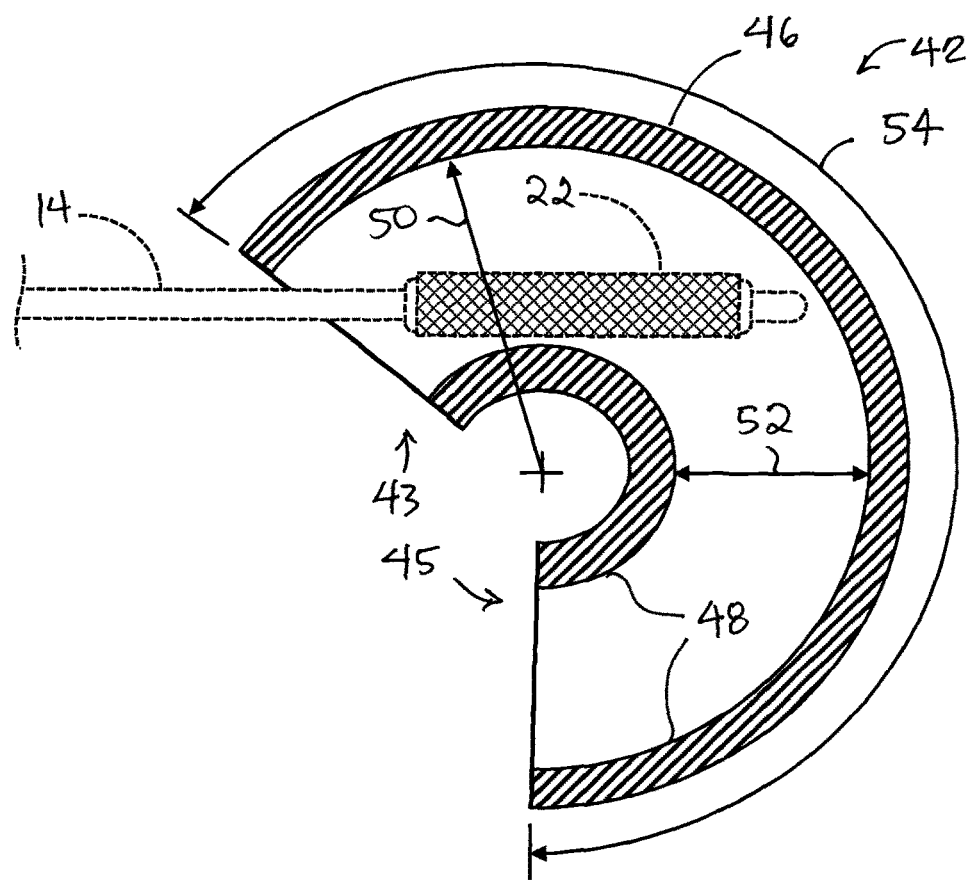

If arc degree 54 in FIG. 7A were modified to be greater as shown in FIG. 7B, then inner surface 48 of turn 46 would force scaffold 22 to bend while traveling through turn 46. In FIG. 7B, arc degree 54 is about 230 degrees. Curvature radius 50 and inner diameter 52 (both of which are the same as in FIG. 7A) and arc degree 54 (which is greater than in FIG. 7A) are sized such that scaffold 22 must bend along its longitudinal axis in order for catheter 14 and endoprosthesis 12 to travel completely through the 230 degree arc of turn 46.

As discussed above, FIGS. 5, 6B and 7B are examples in which curvature radius 50, inner diameter 52, and arc degree 54 are sized such that scaffold 22 must bend along its longitudinal axis in order for catheter 14 and endoprosthesis 12 to move through turn 46. Scaffold 22 may be forced to bend due to contact between scaffold 22 and inner surface 48 of turn 46, and/or contact between endoprosthesis 12 and inner surface 48 of turn 46 and/or contact between catheter 14 and inner surface 48 of turn 46.

Figure 8:
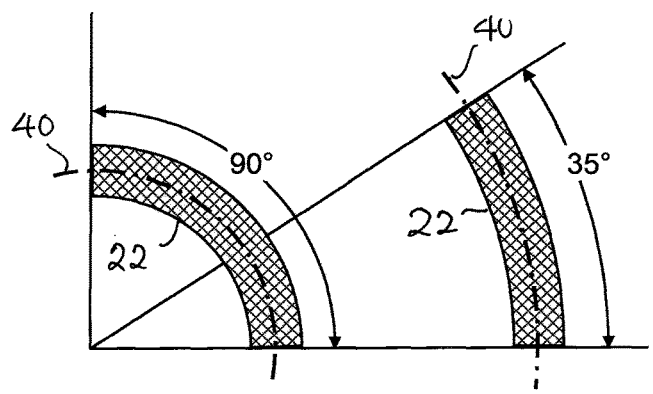
FIG. 8 is a schematic view of two exemplary scaffolds with different amounts of flexing.

Referring to FIG. 8, the amount of bending of scaffold 22 may be measured by the arc degree formed by longitudinal axis 40 of scaffold 22 as measured from opposite ends of scaffold 22. Scaffold 22 on the left side of FIG. 8 is bent to an arc degree of 90 degrees. Scaffold 22 on the right side of FIG. 8 is bent to an arc degree of about 35 degrees. It is to be understood that the curved longitudinal axis 40 of scaffold 22 may, in some cases, not be a perfectly circular arc. In those cases, measurement of the arc degree may be taken from a perfectly circular arc that best fits the curved longitudinal axis of the scaffold. Best fit can be determined from numerical computation, such as least squares and other methods, known in the art.

Excessive bending of scaffold 22 is not desired as this may weaken scaffold 22. In some embodiments, scaffold 22 is forced to bend to an arc degree from 10 degrees to 90 degrees, more narrowly from 30 degrees to 90 degrees, and more narrowly from 30 degrees to 60 degrees. The amount of bending that is suitable for a particular scaffold may depend upon the total mass of the scaffold, the total surface area of the scaffold, the particular arrangement of struts of the scaffold, dimensions of the struts, the polymer material of the scaffold substrate, the level of flexibility that is desired in the scaffold, and/or other factors.

A method of conditioning endoprosthesis 12 prior to use within a patent includes causing scaffold 22 to bend along longitudinal axis 40 of scaffold 22. Preferably, the process is performed in a manner that maintains sterility of scaffold 22, such as by using conditioning tube 42 which has previously been sterilized. For example, the method may include opening a sterilized package which contains endoprosthesis 12 (and optionally containing conditioning tube 42), and then causing scaffold 22 to bend while in a surgical room or similarly clean environment. This process could be performed in a room that is separate from a surgical room in which the patient is located. When conditioning is completed, scaffold 22 can be brought to the patient.

The user pushes and/or pulls scaffold 22 through turn 46 of conditioning tube 42. The user may accomplish this by pushing or pulling proximal segment 16 of catheter 14 so that distal segment 18 of catheter 14 and endoprosthesis 12 are forced to travel through turn 46 of conditioning tube 42. Thereafter, when conditioning is completed, distal segment 18 with balloon 20 and scaffold 22 (mounted on balloon 20) are brought to the patient.

In some cases, endoprosthesis 12 need not be mounted to a catheter. In such cases, endoprosthesis 12 may be forced through turn 46 of conditioning tube 42 by use of a flexible plunger which has previously been sterilized. The user manipulates the flexible plunger to push endoprosthesis 12 through turn 46.

Alternatively, endoprosthesis 12 may be forced through turn 46 of conditioning tube 42 by use of a flexible rod which has previously been sterilized. The user inserts the flexible rod through lumen 38 of endoprosthesis 12. Endoprosthesis 12 is fixed on a forward end of the flexible rod, and then the user may push and/or pull a rear end of the flexible rod so that endoprosthesis 12 is forced to travel through turn 46 of conditioning tube 42.

The conditioning method optionally includes placing scaffold 22 in contact with a sterile liquid before causing the scaffold to bend. Without intending being bound by theory, it is believed that contact with liquid results in hydration of the bioresorbable polymer material of substrate 26, which increases flexibility of scaffold 22. Hydration occurs when substrate 26 absorbs some of the liquid below substrate surface 27 (FIG. 3). Increased flexibility via hydration may facilitate subsequent insertion of endoprosthesis 12 through narrow and tortuous anatomical lumen of the patient. A suitable liquid may be sterilized water, sterilized saline solution, or other aqueous solution.

The temperature of the liquid when in contact with scaffold 22, referred to as the soak temperature, can be at room ambient temperature, normal body temperature, approximate human body temperature, or any temperature from 20° C. to 39° C. (from 68° F. to 102° C.). Preferably, the soak temperature is at normal or approximate human body temperature. When the patient is human, using a soak temperature at normal or approximate human body temperature provides the advantage of bringing scaffold 22 near or at the environmental condition in which scaffold 22 was designed to function. The selected soak temperature may depend upon the total mass of the scaffold, the total surface area of the scaffold, the particular arrangement of struts of the scaffold, dimensions of the struts, the polymer material of the scaffold substrate, the level of flexibility that is desired in the scaffold, and/or other factors.

Room ambient temperature, as used herein, is any temperature from 20° C. to 26° C. (from 68° F. to 79° F.). Normal human body temperature, as used herein, is 37.0° C. (98.6° F.). Approximate human body temperature, as used herein, is any temperature from 35° C. to 39° C. (95° F. to 102° F.).

The amount of time in which endoprosthesis 12 remains in contact with water should be limited to avoid the possibility of an increase in the scaffold physical profile (as measured by outer diameter 34 or inner diameter 36 of scaffold 22), a decrease in scaffold retention onto its delivery device (such as balloon 20), and/or drug release from coating 28. An increase in scaffold dimension may make it more difficult to deliver the scaffold through anatomical lumen. A decrease in scaffold retention should be avoided to insure that the scaffold does not slip off its delivery device. Drug release during the conditioning process should be avoided to insure that the desired drug release profile (as measured by the amount of drug released versus time after the scaffold is implanted) is not adversely affected.

The amount of time, referred to as soak period, can be from 1 minute to 10 minutes, more narrowly from 1 minute to 5 minutes, or more narrowly from 1 minute to 2 minutes. The selected amount of time may depend upon the total mass of the scaffold, the total surface area of the scaffold, the particular arrangement of struts of the scaffold, dimensions of the struts, the polymer material of the scaffold substrate, the level of flexibility that is desired in the scaffold, and/or other factors.

Figure 9:
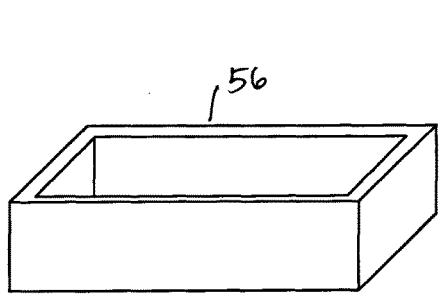
FIG. 9 is a perspective view of an exemplary container for exposing a scaffold to liquid.

Placing scaffold 22 in contact with the liquid may be performed by placing endoprosthesis 12 in a sterile container of the liquid. Any type of container could be used. The sterile container could be a bag or tray 56, as shown in FIG. 9. The type of container may depend on the size of endoprosthesis 12 and/or whether endoprosthesis 12 is solitary or is attached to a catheter. The user adds sterile liquid (at the desired soak temperature) to the container, and then endoprosthesis 12 is placed in the container. Endoprosthesis 12 is removed from the container at the end of the soak period. Thereafter, the method proceeds by causing the scaffold to bend as described herein.

In some cases, endoprosthesis 12 may arrive in its own sterile carrier, such as a bag or carrier tube. For example, a catheter with an endoprosthesis may be placed by a manufacturer in a carrier tube to prevent damage to the catheter and endoprosthesis during transportation. Preferably, the carrier tube is sterilized to the same level of sterility as catheter 14 and endoprosthesis 12 since catheter 14 and endoprosthesis 12 will come into contact with the carrier tube prior to introduction of catheter 14 and endoprosthesis 12 within a human or animal patient.

Figure 10:
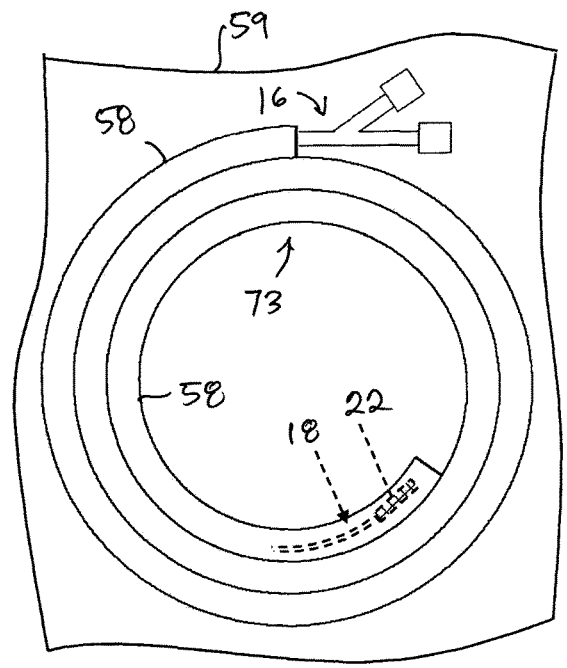
FIG. 10 is a schematic view of an exemplary sterilized package containing a coiled tube which carries a catheter and a scaffold.

The carrier tube may be a straight tube or coiled tube, as shown in FIG. 10. A straight tube may be used with relatively short catheters, and a coiled tube may be used with relatively long catheters. Placing scaffold 22 in contact with the liquid may be performed by introducing water to the bag, carrier tube, or other container in which endoprosthesis 12 has been placed by the manufacturer. At the end of the soak period, the liquid is drained from the container and/or endoprosthesis 12 is removed from the container. Thereafter, the method proceeds by causing the scaffold to bend as described herein.

The coiled tube may differ from what is illustrated herein. For example, the coiled tube may be configured as described in U.S. Application Publication No. 2014/0379064, FIG. 6A.

Referring again to FIG. 10, endoprosthesis 12 may arrive within its own sterile carrier which is in the form of coiled tube 58. A portion of proximal segment 16 of catheter protrudes out of one end of coiled tube 58. Distal segment 18 and endoprosthesis 12 are fully contained within the opposite end of coiled tube 58. The sterile carrier (coiled tube 58) may optionally arrive within sterilized package 59. Sterilized package 59 may be in the form of a bag or pouch made of metallic foil, a sheet of high-density polyethylene fibers (such as Tyvek®), a film of polyethylene terephthalate glycol-modified (PETG), and/or other materials known in the art of medical packaging. One side of sterilized package 59 may be optically transparent, as shown in FIG. 10, so that its contents are visible. Sterilized package 59 can be tray 56 (FIG. 9) covered with a sheet or film of material adhered on the top edges of tray 56.

Sterilized package 59 containing endoprosthesis 12 (and optionally containing conditioning tube 42 and/or tray 56) may be sterilized according to any suitable method known in the art, such as by a gas, gamma radiation, or electron beam radiation. Sterilized package 59 is sealed to maintain sterility of its contents. The user must break the seal in order to remove endoprosthesis 12 from sterilized package 59.

Figure 11:
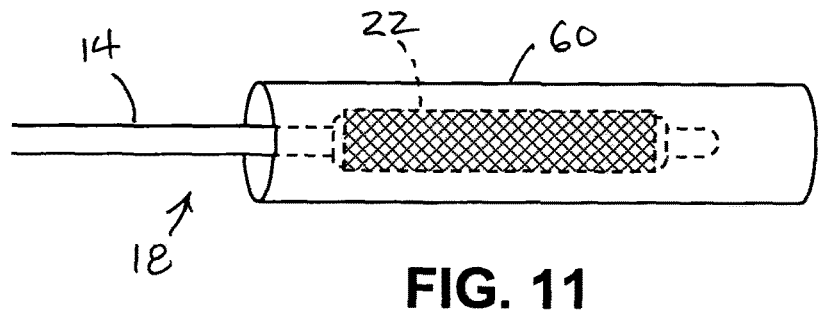
FIG. 11 is a schematic view of an exemplary sheath covering a scaffold.

As shown in FIG. 11, endoprosthesis 12 may arrive with sheath 60 covering scaffold 22. Sheath 60 is a tube designed to be removed from endoprosthesis 12 before endoprosthesis 12 is implanted within a patient. Sheath 60 may serve to protect scaffold 22 from damage prior to implantation. In cases where scaffold 22 has been crimped onto balloon 20 of catheter 14, sheath 60 may serve to constrain scaffold 22 in a crimped state. The user may remove sheath 60 by sliding sheath 60 off endoprosthesis 12.

Figure 12A:
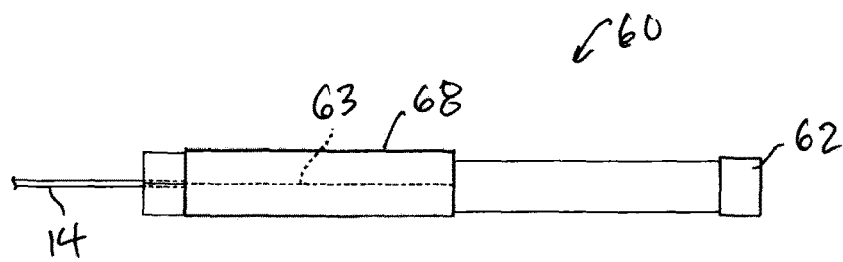
FIGS. 12A-12C are schematic views of another exemplary sheath covering a scaffold.
Figure 12B:
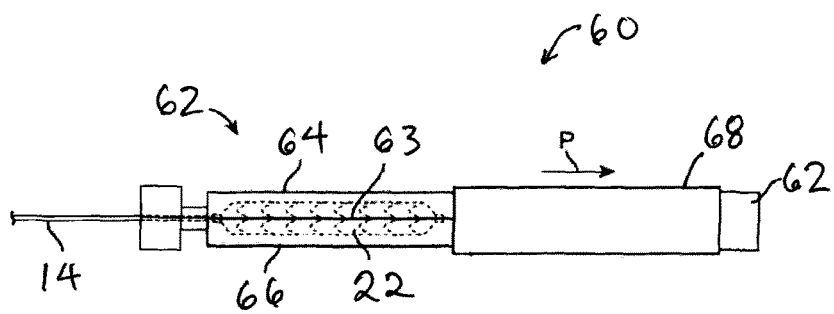
Figure 12C:
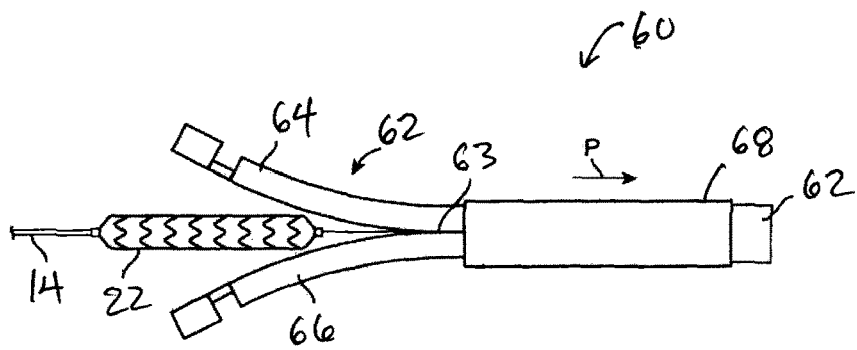

Other types of sheaths are possible. For example, sheath 60 can be in the form of a sheath pair, as described in U.S. Pat. No. 8,414,528, which is incorporated herein by reference. As shown in FIGS. 12A-12C, the sheath pair includes inner sheath 62 which contacts and constrains scaffold 22 in a crimped state. Inner sheath 62 includes slit 63 defining upper and lower sections 64, 66 of inner sheath 62. Upper and lower sections 64, 66 constrain scaffold 22 in a crimped state. Upper and lower sections 64, 66 are biased to spread apart from each other at slit 63. The sheath pair includes outer sheath 68 disposed over the inner sheath 62 and which keeps upper and lower sections 64, 66 together. The user may remove sheath 60 by first pulling outer sheath 68 in the direction of arrow P while inner sheath 62 and scaffold 22 remain in place. Pulling outer sheath 68 relative to inner sheath 62 and scaffold 22 allows upper and lower sections 64, 66 of inner sheath 62 to spread apart and lift away from scaffold 22, as shown in FIG. 12C. Next, the user may pull both inner sheath 62 and outer sheath 68 away from scaffold 22.

As discussed above, placing scaffold 22 in contact with liquid may increase flexibility of scaffold 22 prior to use within a patient. Removal of sheath 60 may increase contact between scaffold 22 and the liquid. Removal of sheath 60 from around scaffold 22 may be performed at a time between opening sterilized package 59 (FIG. 10) and placing the scaffold in contact with liquid. Alternatively, removal of sheath 60 from around scaffold 22 may be performed at a time between placing the scaffold in contact with the liquid and causing the scaffold to bend.

As discussed above, opening of sterilized package 59 may include breaking a seal of a pouch containing scaffold 22. The pouch and scaffold are sterilized prior to the breaking of the seal. Removing scaffold 22 from sterilized package 59 may be performed at a time between breaking of the seal and placing the scaffold in contact with the liquid. In this case, sterilized package 59 may be opened, and then scaffold 22 is removed from sterilized package 59. Next, scaffold 22 may be placed in container 56 (FIG. 9) filled with liquid, or liquid may be introduced into coiled tube 58 (FIG. 10).

Alternatively, removing scaffold 22 from sterilized package 59 (FIG. 10) may be performed at time between placing the scaffold in contact with liquid and causing the scaffold to bend. In this case, sterilized package 59 may be opened, and then water may be added to sterilized package 59 while scaffold 22 remains in sterilized package 59.

Figure 13:
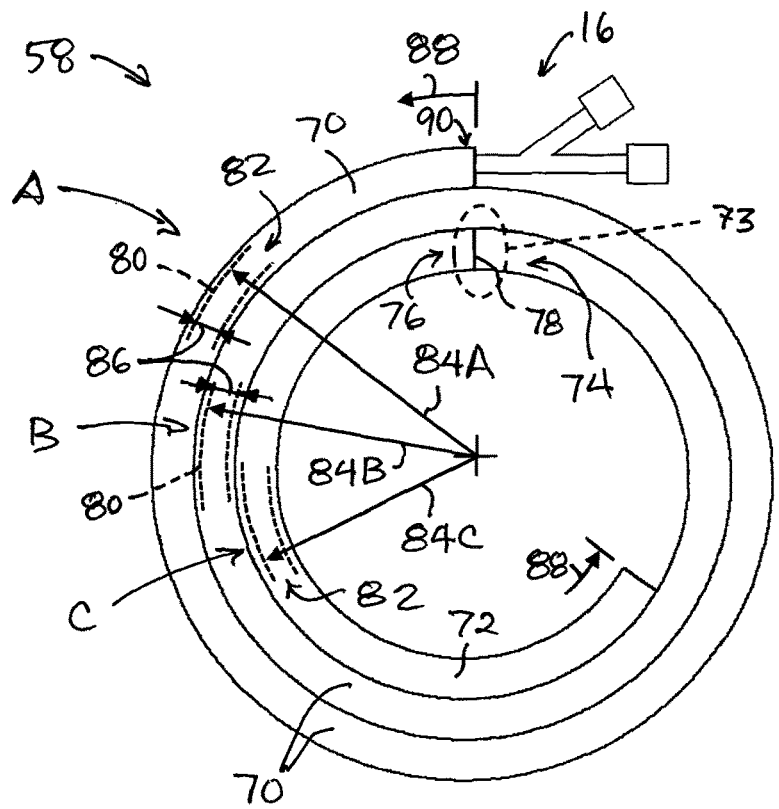
FIG. 13 is a schematic plan view of an exemplary coiled tube which carries a catheter and a scaffold.
Figure 14A:
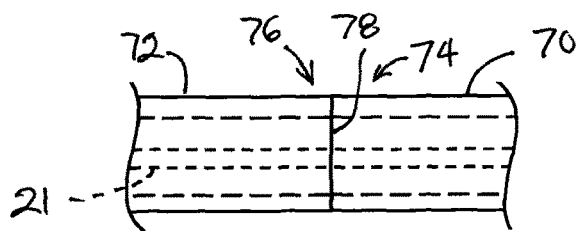
FIGS. 14A and 14B are schematic views showing alternative configurations for a coupling region in FIG. 13.

Referring to FIG. 13, coiled tube 58 (a carrier tube) may include a first segment 70 and a second segment 72. Catheter body 21 extends from first segment 70 to second segment 72. First segment 70 contains proximal segment 16 of catheter 14. Second segment 72 contains distal segment 18 of catheter 14 and endoprosthesis 12. At coupling region 73, terminal end 74 of first segment 70 is attached to terminal end 76 of second segment 72. As shown in FIG. 14A, terminal ends 74, 76 abut to form interface seam 78. Alternatively, terminal ends 74, 76 may be spaced apart as shown in FIG. 14B.

Figure 14B:
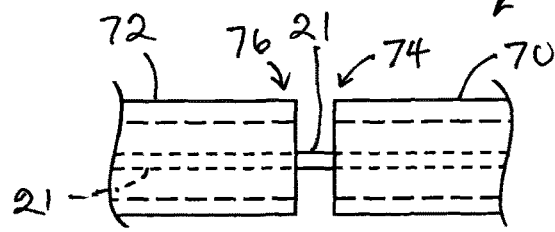

FIGS. 14A and 14B show alternative configurations for coupling region 73 in FIG. 13. In FIGS. 14A and 14B, terminal ends 74, 76 face directly toward each other. Terminal ends 74, 76 may be attached to each other by coupler 78 as shown in FIG. 15. Coupler 78 is a tube that engages terminal ends 74, 76, such as by friction, and allows terminal ends 74, 76 to be pulled apart so as to detach second segment 72 from first segment 70 without damaging first segment 70. The coupler can be configured in other ways. For example, the coupler can be a clip or clamp.

Referring again to FIG. 13, coiled tube 58 has coil inner surface 80 defining internal passageway 82 within coiled tube 58. Internal passageway 82 through first segment 70 and second segment 72. Internal passageway 82 extends from rear end 90 of first segment 70 to forward end forward end 92 of second segment 72. Catheter body 21 (FIG. 1) and endoprosthesis 12 are contained within internal passageway 82. Internal passageway 82 has radius of curvature 84, coil inner diameter 86, and coil arc degree 88. Coil inner diameter 86 is greater than outer diameter 34 of scaffold 22. The radius of curvature of coiled tube 58 is referred to herein as the coil curvature radius. Since coiled tube 58 is a spiral, coil curvature radius 84 at one section of coiled tube 58 differs from another section of coiled tube 58. At each section of coiled tube 58, coil curvature radius 84 is measured from a point outside of internal passageway 82 to an outermost portion or point of coil inner surface 80 of passageway 82. For example, sections A, B and C of coiled tube 57 have coil curvature radii 84A, 84B, and 84C. Coil curvature radius 84A is greater than coil curvature radius 84B, which is greater than coil curvature radius 84C.

All coil curvature radii 84 of coiled tube 58 are greater than curvature radius 50 of each turn 46 of conditioning tube 42 (FIGS. 5, 6A, 7A, and 17). Optionally, coil curvature radii 84, coil inner diameter 86, and coil arc degree 88 are sized such that scaffold 22 does not bend along its longitudinal axis 40 (FIG. 1) in order for catheter 14 and endoprosthesis 12 to travel through the entire internal passageway 82 of coiled tube 58.

Coil arc degree 88 is measured from rear end 90 of first segment 70 of coiled tube 58 to forward end 92 of second segment 72 of coiled tube 58. In FIG. 13, first segment 70 makes three complete revolutions or loops, which forms an arc of 1080 degrees. Second segment 72 forms an arc of about 240 degrees. Therefore, coil arc degree 88 of internal passageway 82 is about 1320 degrees.

The coil arc degree of internal passageway 82 may be lesser or greater than what is illustrated herein. For example, the coiled tube for a relatively short catheter may require a smaller coil arc degree. The coiled tube for a relatively long catheter may require a greater coil arc degree so that it can fit within sterilized package 59 (FIG. 10). The coil arc degree of coiled tube 58 can be at least 360 degrees (one loop), at least 540 degrees, or at least 720 degrees (two loops).

The connection between first and second segments 70, 72 of coiled tube 58 at coupling region 73 (FIG. 13) may be accomplished in various ways. FIG. 16 shows an exemplary configuration for coupling region 73. Terminal end 74 of first segment 70 may be disposed around terminal end 76 of second segment 72. Terminal end 74 fits tightly around and frictionally engages terminal end 76. The frictional engagement allows second segment 72 to remain attached to first segment 70 while still allowing a user to pull second segment 72 apart from first segment 70 without damaging first segment 70.

Alternatively, the geometry of FIG. 16 may be reversed such that terminal end 74 of first segment 70 is received within terminal end 76 of second segment 72.

FIG. 17 shows another conditioning tube 42. Conditioning tube 42 includes straight segment 94 followed by three turns 46A, 46B, and 46C. Each turn has an arc degree of about 180 degrees. Also, each turn extends in a direction that is different from an adjacent turn. When viewed from the left, turn 46A forms a 180-degree convex arc, which is followed by turn 46B that forms a 180-degree concave arc, which is followed by turn 46C that forms a 180-degree convex arc. Thus, turn 46B extends in a direction opposite of turns 46A and 46C. Having multiple turns in different directions helps to ensure that various sides of scaffold 22 are flexed under compression and tension. In turn 46A, one side 96 of scaffold 22 is flexed under tension while the opposite side 98 of scaffold 22 is flexed under compression. When scaffold 22 travels into turn 46B, side 96 is flexed under compression while side 98 is flexed under tension.

Conditioning tube 42 has two terminal ends 43, 45. Terminal ends 43, 45 are detached from coiled tube. Either one of the terminal ends 43, 45 is configured to be attached to terminal end 74 of first segment 70 of coiled tube 58 at coupling region 73 (FIG. 13). Either one of the terminal ends 43, 45 may be configured as shown for terminal end 76 of second segment 72 in FIG. 14A, 14B, or 16.

Figure 18A:
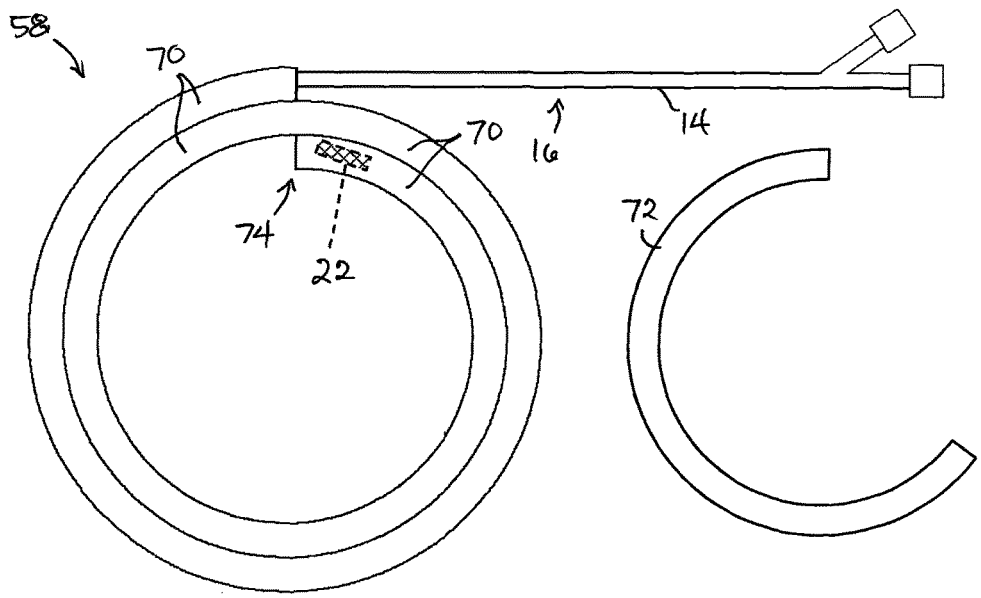
FIGS. 18A and 18B are schematic plan views showing an exemplary method of using the coiled tube of FIG. 13 with the conditioning tube of FIG. 17.
Figure 18B:
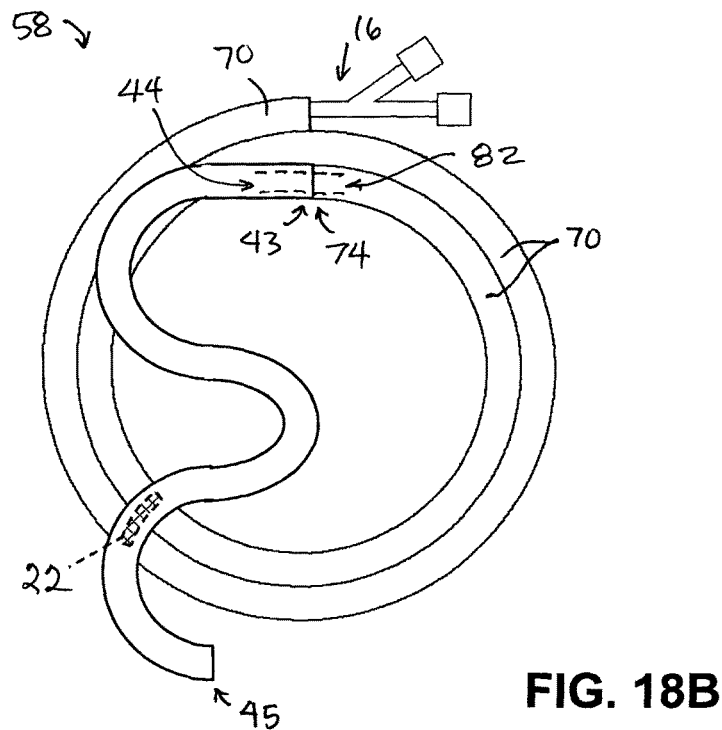

FIGS. 18A-18B illustrate an exemplary method of using conditioning tube 42 of FIG. 17. First, the user pulls proximal end 16 of catheter 14 partially out of first segment 70 such that scaffold 22 moves from second segment 72 to first segment 70 of coiled tube 58 (a carrier tube). Pulling may be performed at a time after opening of sterilized package 59 (FIG. 10). Next, the user detaches second segment 72 from first segment 70 while proximal end 16 of catheter 14 remains partially out of first segment 70. FIG. 18A shows first segment 70 after second segment 72 has been removed, which exposes terminal end 74 of first segment 70. Next, the user attaches terminal end 43 of conditioning tube 42 to terminal end 74 of first segment 70. Conditioning tube 42 has replaced second segment 72 such that first segment 70 is now attached to conditioning tube 42. Passageway 44 of conditioning tube 42 meets internal passageway 82 of first segment 70. Next, the user pushes proximal end 16 of catheter 14 back into first segment 70 such that scaffold 22 moves through at least one turn of the passageway within conditioning tube 42. FIG. 18B shows the position of scaffold 22 within conditioning tube 42 after the user has pushed proximal end 16 of catheter 14 back into first segment 70.

In FIG. 18B, conditioning tube 42 is illustrated as overlapping portions of coiled tube 58. Conditioning tube 42 is disposed on top of portions of first segment 70 of coiled tube 58, and conditioning tube 42 does not obstruct any portion of internal passageway 82 of first segment 70.

Optionally, sheath 60 may be disposed over scaffold 22. In such as case, the user may remove sheath 60 before the above-described step of attaching terminal end 43 of conditioning tube 42 to terminal end 74 of first segment 70 of coiled tube 58. Before attaching conditioning tube 42 to first segment 70, the user may push proximal segment 16 of catheter 14 slightly so that sheath 60 extends outside of terminal end 74 of first segment 70. With sheath 60 exposed in this way, the user may then remove sheath 60 from scaffold 22. Thereafter, the user attaches conditioning tube 42 to first segment 70. If necessary, the user may pull catheter 14 back into first segment 70 before attaching conditioning tube 42 to first segment 70.

Optionally, scaffold 22 is placed in contact with sterile liquid (not a bodily fluid) in order to hydrate substrate 26 of scaffold 22. The user may introduce the liquid into coiled tube 58 after sheath 60 is removed from scaffold 22 in order to maximize contact with liquid. In addition or alternatively, coiled tube 58 may be placed into tray 56 (FIG. 9) or other container filled with the liquid. Alternatively, sheath 60 may be removed after placing scaffold 22 in contact with the liquid.

In alternative aspects, conditioning tube 42 may already be attached to first segment 70 of coiled tube 58. In such a case, the user does not need to performed the above-describe step of attaching conditioning tube 42 to coiled tube 58. For example, when opening sterilized packaged 59 (FIG. 10), conditioning tube 42 may have already been attached to region 73 of coiled tube 58.

Figure 19A:
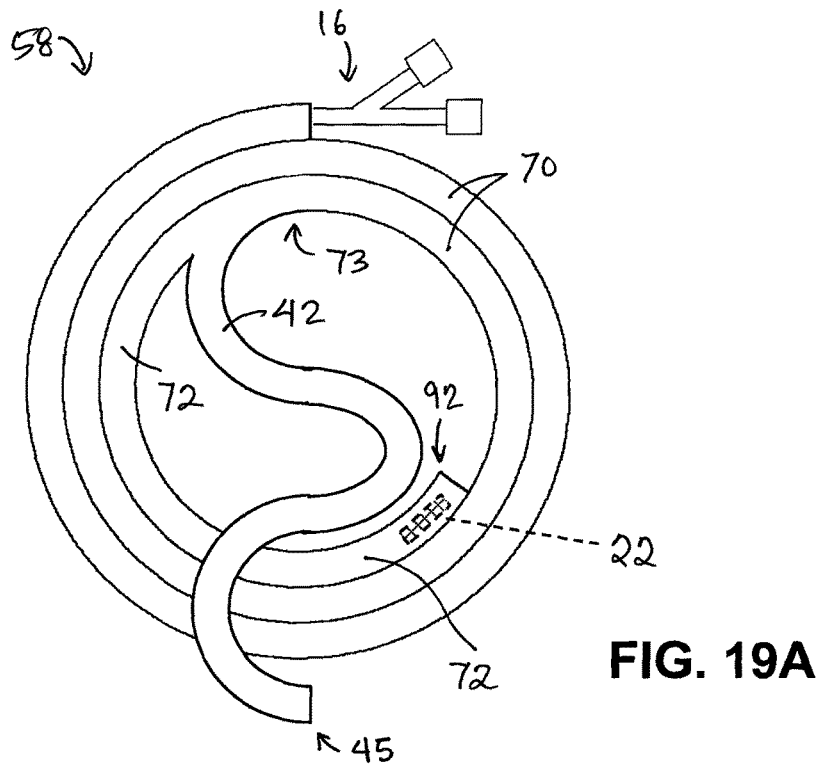
FIGS. 19A-19D are schematic plan views showing an exemplary method of using a coiled tube with the conditioning tube of FIG. 17 already attached thereto.

FIGS. 19A-19D illustrate an exemplary method of using conditioning tube 42 which has already been attached to coupling region 73 of coiled tube 58 (a carrier tube). FIG. 19A shows system 10 at a time when sterilized packaged 59 is opened. Endoprosthesis 22 is located within second segment 72 of coiled tube 58. Conditioning tube 42 is illustrated as overlapping portions of coiled tube 58. Conditioning tube 42 is disposed on top of portions of coiled tube 58, and conditioning tube 42 does not obstruct any portion of the internal passageway of coiled tube 58.

Figure 19B:
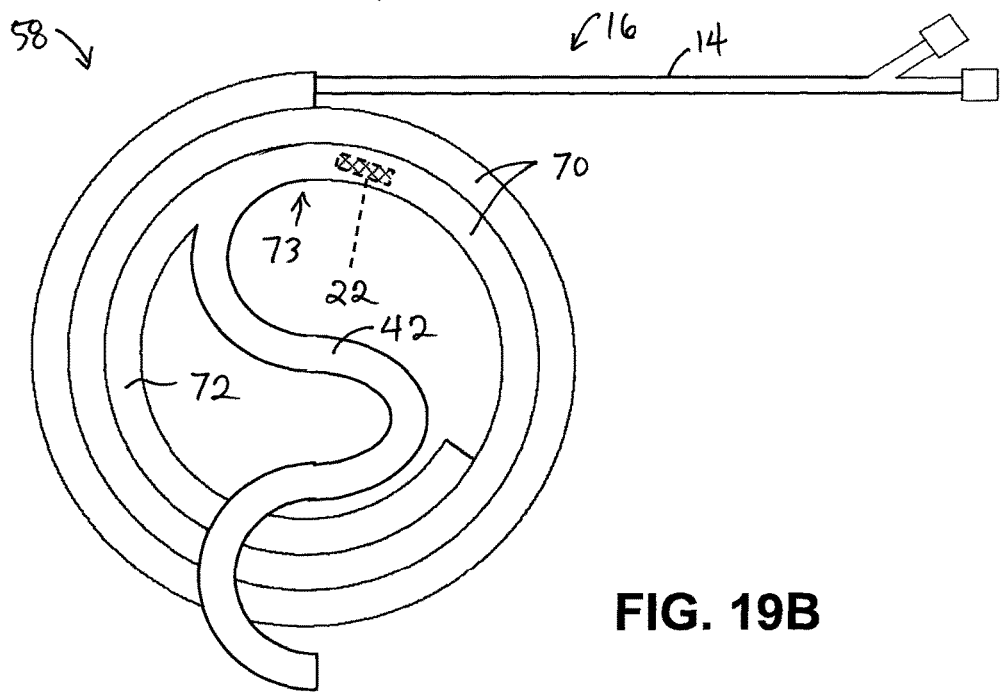
Figure 19C:
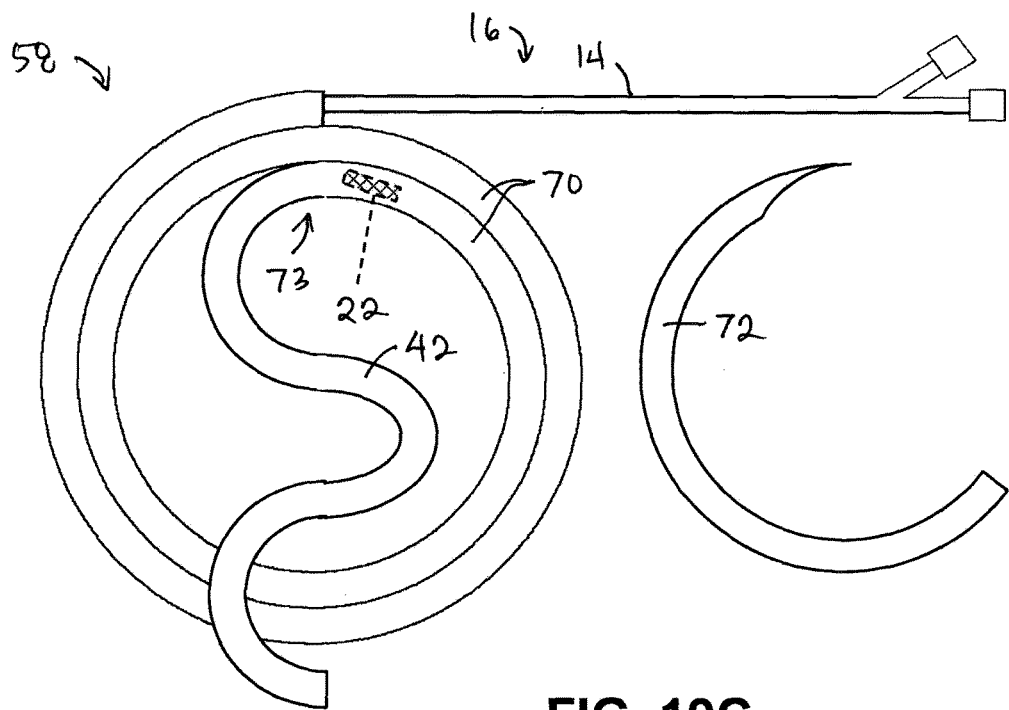
Figure 19D:
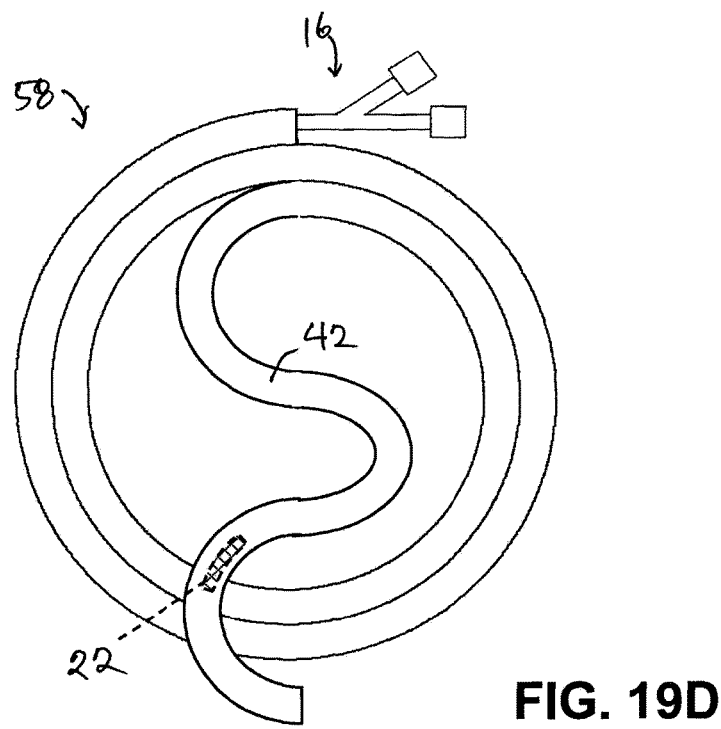

After removing system 10 from sterilized packaged 59, the user pulls proximal segment 16 of catheter 14 partially out of first segment 70 of coiled tube 58. This causes scaffold 22 to move from second segment 72 to first segment 70, as shown in FIG. 19B. Next, the user detaches second segment 72 from first segment 70, as shown in FIG. 19C. Next, the user pushes proximal segment 16 of catheter 14 back into first segment 70 such that scaffold 22 moves through at least one turn of the passageway within conditioning tube 42, as shown in FIG. 19D.

Optionally, sheath 60 may be disposed over scaffold 22 in FIG. 19A. In such as case, the user may remove sheath 60 before scaffold 22 is forced through the passageway within conditioning tube 42. The user may remove sheath 60 by pushing proximal segment 16 of catheter 14 slightly so that sheath 60 extends slightly outside of forward end 92 (FIG. 19A) of coiled tube 58. With sheath 60 exposed in this way, the user may then remove sheath 60 from scaffold 22. Thereafter, the user performs the steps described for FIGS. 19B-19D.

Optionally, scaffold 22 is placed in contact with sterile liquid (not a bodily fluid) in order to hydrate substrate 26 of scaffold 22. The user may introduce the liquid into coiled tube 58 after sheath 60 is removed from scaffold 22 in order to maximize contact with liquid. In addition or alternatively, coiled tube 58 may be placed into tray 56 (FIG. 9) or other container filled with the liquid. Alternatively, sheath 60 may be removed after placing scaffold 22 in contact with the liquid.

Figure 20A:
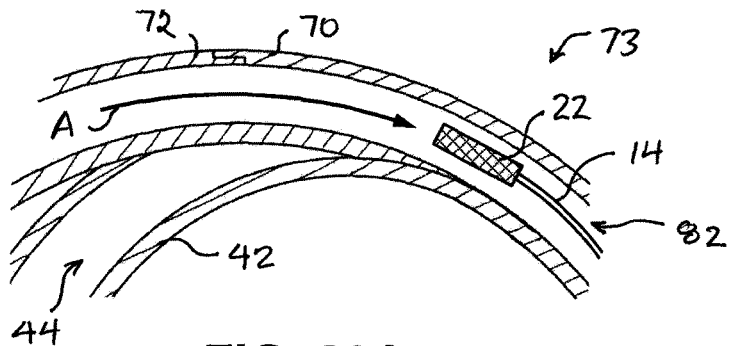
FIGS. 20A and 20B are cross-section views showing an exemplary configuration for a connection region in FIGS. 19B and 19C.
Figure 20B:
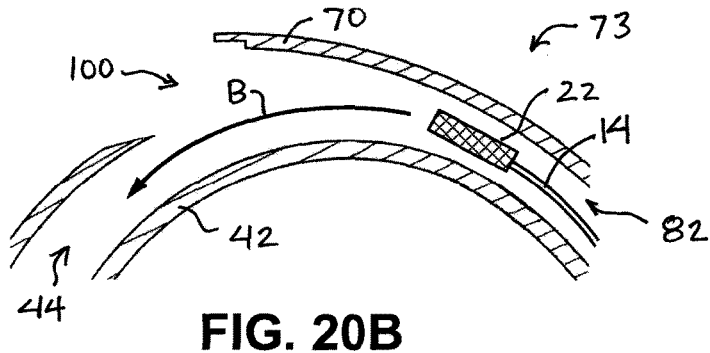

Coupling region 73 in FIG. 19A may be configured in various ways. As shown in FIGS. 20A-20B for example, second segment 72 may obstruct passageway 44 of conditioning tube 42. When second segment 72 remains attached to first segment 70, there is no way for scaffold 22 to enter passageway 44 of conditioning tube 42, as shown in FIG. 20A. Passageway 44 of conditioning tube 42 does not meet or intersect internal passageway 82 of coiled tube 58. The user may pull proximal segment 16 (FIG. 19A) of catheter 14 such that scaffold 22 enters internal passageway 82 of first segment 70, as indicated by the arrow A in FIG. 20A.

When second segment 72 has been detached from first segment 70, passageway 44 of conditioning tube 42 is no longer obstructed as shown in FIG. 20B. Passageway 44 of conditioning tube 42 meets or intersects internal passageway 82 of first segment 70. Removal of second segment 72 leaves aperture 100 between first segment 70 and conditioning tube 42. Aperture 100 may allow the user to remove sheath 60 from scaffold 22. Aperture 100 may also allow the user to place scaffold 22 in contact with liquid. Next, the user may push proximal segment 16 (FIG. 19C) of catheter 14 such that scaffold 22 enters conditioning tube 42, as indicated by the arrow B in FIG. 20B. Optionally, before pushing proximal segment 16 of catheter 14, the user may place a cover over aperture 100 to guide scaffold 22 into passageway 44 of conditioning tube 42.

The user may repeat the flexing procedure. For example, after scaffold 22 arrives at its position shown in FIG. 18B or 19D, the user may pull catheter 14 again to bring scaffold 22 to the position shown in FIG. 18A or 19C. Next, the user pushes catheter 14 again to bring scaffold 22 to the position shown in FIG. 18B or 19D. Pulling and pushing may be repeated any number of times, as appropriate. Prior to use of endoprosthesis 12 within the patient, the user pulls pull catheter 14 and endoprosthesis 12 completely out of conditioning tube 42 and coiled tube 58.

A method of using an endoprosthesis may include conditioning the endoprosthesis prior to use within a patient as described herein, following by introducing the conditioned endoprosthesis in the patient. Introduction of the conditioned endoprosthesis may be accomplished by inserting catheter 14 and endoprosthesis 12 in an anatomical lumen of the patient according to methods known in the art. Next, the user manipulates catheter 14 to deliver endoprosthesis 12 to an intended implantation site. Next, the user may allow scaffold 22 of endoprosthesis 12 to self-expand. Alternatively, the user may forcibly expand scaffold 22 by inflating balloon 20 of catheter 14. Next, the user may withdraw catheter 14 from the patient while leaving endoprosthesis 12 including scaffold 22 at the implantation site.

As mentioned above, the sterile carrier for catheter 14 and endoprosthesis 12 may be a carrier tube. The carrier tube may be a coiled tube (as shown for example in FIGS. 10, 13, 18A-18B, and 19A-19D) or a straight tube. For a straight tube, first segment 70 and second segment 72 of coiled tube 58 would be replaced with first and second segments that are straight. As compared to curved segments 70 and 72, the straight segments would function in the same way and be structurally the same except for being straight. The straight segments may be suitable for relatively short catheters. Also, straight segments may be used when having a very long sterilized package 59 (FIG. 10) is not a major concern.

The carrier tube, whether it is coiled tube 58 or a straight tube, may be made of any suitable material that can be sterilized and is preferably biocompatible. The same applies to conditioning tube 42. The material used for the carrier tube (such as coiled tube 58) and conditioning tube 42 may be metal, including without limitation stainless steel or other metals suitable for medical environments. For economy and ease of manufacture, the material used may be polymer, including without limitation low density polyethylene, polycarbonate, or other polymer suitable for medical environments. The selected material allows conditioning tube 42 to maintain its shape (curvature radii, inner diameter, and arc degree) when scaffold 22 is moved through turns 46. Optionally, structural bracing (such as clips or straps) may be attached to the carrier tube and/or the conditioning tube so that the tubes maintain their shape (curvature radii, inner diameter, and arc degree).

As shown in FIGS. 18B and 19A, terminal end 45 of conditioning tube 42 extends beyond the outermost perimeter of coiled tube 58. That is, conditioning tube 42 extends outside of the foot print of coiled tube 58 as viewed in plan view. In this context, a "plan view" is a view taken along an axis perpendicular to the plane of coiled tube 58.

Alternatively, the conditioning tube may be shorter or configured differently that what is illustrated such that terminal end 45 does not extend beyond the outermost perimeter of coiled tube 58. This allows conditioning tube 42 to be entirely within the foot print of coiled tube 58 as viewed in plan view. Thus, conditioning tube 42 may be added to already existing packaging, such as sterilized package 59 (FIG. 10), which having to alter the size of the packaging.

As mentioned above, substrate 26 is formed of a bioresorbable polymer material. The bioresorbable polymer material may be poly(lactic acid) or a polymer based on poly(lactic acid). Polymers based on poly(lactic acid) include graft copolymers, block copolymers, such as AB block-copolymers ("diblock-copolymers") or ABA block-copolymers ("triblock-copolymers"), and mixtures thereof. Examples of bioresorbable polymer materials include without limitation poly(lactide-co-glycolide), poly(glycolic acid), poly(glycolide), poly(L-lactic acid), poly(L-lactide) (PLLA), poly(D,L-lactic acid), and poly(caprolactone) (PCL) copolymers. As further examples, substrate 26 can be made from a PLLA/PCL copolymer. The bioresorbable polymer material of substrate 26 may be a material selected from the group consisting PLLA, poly(L-lactide-co-glycolide) ("PLGA"), poly(D,L-lactide-co-glycolide), poly(L-lactide-co-caprolactone), poly(glycolide-co-caprolactone) and poly(L-lactide-co-D-lactide) ("PLLA-co-PDLA").

Coating 28 that is optionally applied on substrate 26 can include a polymer, examples of which include without limitation poly(D, L-lactide) ("PDLLA"), ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol. The polymer of coating 28 optionally carries a drug or other therapeutic agent, as previously mentioned.

Figure 21:
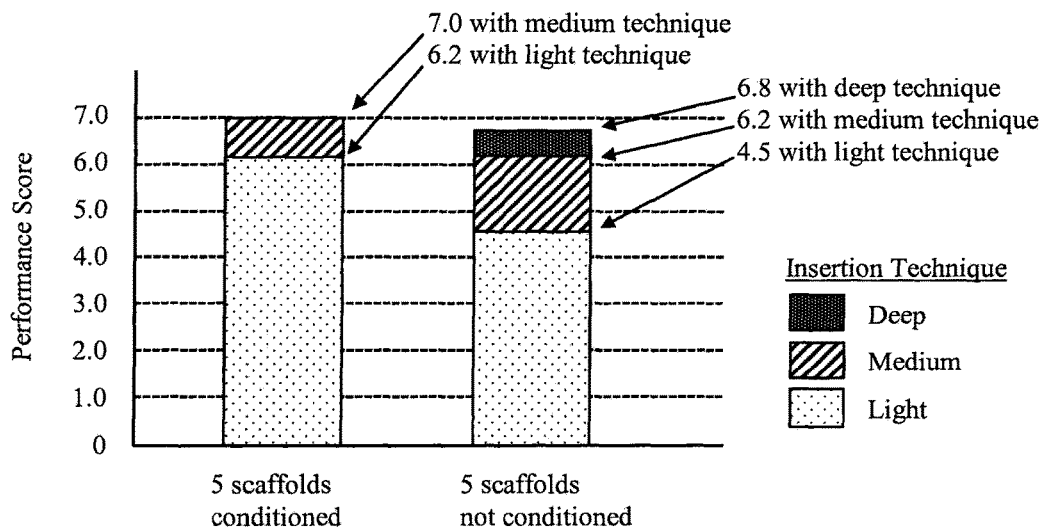
FIG. 21 is a bar graph of test results showing performance of scaffolds that were conditioned and scaffolds that were not conditioned.

FIG. 21 shows results of comparison testing to determine the effectiveness of conditioning of a bioresorbable scaffold. Ten scaffolds were made with a poly(L-lactide) substrate and poly(D,L-lactide) coating. The scaffolds were inserted, using a guide catheter, into a test fixture called a tortuosity model which is intended to simulate an anatomical lumen with diseased areas. The tortuosity model included various bends such as may be encountered in an anatomical lumen. The tortuosity model included various constrictions corresponding to stenosis of an anatomical lumen and calcifications within an anatomical lumen. Insertion of the scaffolds was performed with varying levels of aggressiveness, representing different levels of guide catheter support during a clinical procedure. A "light" insertion technique is the least aggressive, "medium" insertion technique involves an intermediate level of aggressiveness, and a "deep" insertion technique is the most aggressive.

Before insertion into the tortuosity model, five of the scaffolds were conditioned by placing them in contact with an aqueous solution at a temperature from 35° C. to 39° C. (95° F. to 102° F.) and by mechanical flexing of the scaffold. The other five scaffolds were not conditioned prior to insertion into the tortuosity model. Performance was scored according to the distance each scaffold was able to travel through the tortuosity model. A greater numerical score indicates better performance in that the scaffold was able to travel through more bends and constrictions. The greatest possible score was 7.0. A score of 7.0 is achieved when a scaffold exits the tortuosity model after traveling through it completely.

FIG. 21 shows that conditioned scaffolds achieved an average score of about 6.2 when using a light insertion technique. All conditioned scaffolds achieved the maximum score of 7.0 when using a medium insertion technique.

Scaffolds that were not conditioned generally required greater guide catheter support to navigate the bends and constrictions of the tortuosity model. These scaffolds also required greater guide catheter support to reach the furthest point of travel within the tortuosity model. Average scores of 4.5, 6.2, and 6.8 were achieved with light, medium, and deep insertion techniques, respectively. By comparison, the average score for the conditioned scaffolds with a light insertion technique was 6.2, and all conditioned scaffolds were able to exit the tortuosity model (score of 7.0) with a medium insertion technique.

While several particular forms of the invention have been illustrated and described, it will also be apparent that various modifications can be made without departing from the scope of the invention. It is also contemplated that various combinations or subcombinations of the specific features and aspects of the disclosed embodiments can be combined with or substituted for one another in order to form varying modes of the invention. Accordingly, it is not intended that the invention be limited, except as by the appended claims.

What is claimed is:

1. A method for conditioning an endoprosthesis prior to use within a patient, the method comprising:
    opening a sterilized package containing the endoprosthesis, the endoprosthesis including a scaffold having a substrate formed of a bioresorbable polymer material; followed by
    placing the scaffold in contact with a sterile liquid; followed by
    causing the scaffold to bend along a longitudinal axis of the scaffold before the endoprosthesis is used within a patient,
    wherein said causing the scaffold to bend includes moving the scaffold through a passageway within a conditioning tube, said moving includes moving the scaffold through at least one turn of the passageway;
    withdrawing the scaffold out of the passageway of the conditioning tube after said moving the scaffold through the passageway; and
    followed by introducing the endoprosthesis into a human or animal body.

2. The method of claim 1, wherein said placing the scaffold in contact with the liquid includes any one or a combination of:
    introducing the liquid into a carrier tube that contains the scaffold, and
    placing the scaffold into a container of the liquid.

3. The method of claim 1, wherein the endoprosthesis is disposed on a catheter, and said causing the scaffold to bend includes any one or a combination of pushing and pulling the catheter such that the scaffold moves through the at least one turn of the passageway within the conditioning tube.

4. The method of claim 1, wherein a sheath is disposed around the scaffold, and the method further comprises removing the sheath from around the scaffold, said removing performed either (a) at a time between said opening the sterilized package and said placing the scaffold in contact with the liquid or (b) at a time between said placing the scaffold in contact with the liquid and said causing the scaffold to bend.

5. The method of claim 1, wherein said opening of the sterilized package includes breaking a seal of the sterilized package, the sterilized package and scaffold having been sterilized prior to said breaking of the seal, and the method further comprises removing the scaffold from the sterilized package either (a) at a time between said breaking of the seal and said placing the scaffold in contact with the liquid or (b) a time between said placing the scaffold in contact with the liquid and said causing the scaffold to bend.

6. A method for conditioning an endoprosthesis prior to use within a patient, the method comprising:
    opening a sterilized package containing the endoprosthesis, the endoprosthesis including a scaffold having a substrate formed of a bioresorbable polymer material; followed by
    placing the scaffold in contact with a sterile liquid; followed by
    causing the scaffold to bend along a longitudinal axis of the scaffold before the endoprosthesis is used within a patient,
    wherein said causing the scaffold to bend includes moving the scaffold through a passageway within a conditioning tube, said moving includes moving the scaffold through at least one turn of the passageway,
    wherein the endoprosthesis is disposed on a catheter, and said causing the scaffold to bend includes any one or a combination of pushing and pulling the catheter such that the scaffold moves through the at least one turn of the passageway within the conditioning tube,
    wherein the catheter and scaffold are disposed within a carrier tube, the carrier tube includes a first segment and a second segment, the method further comprises:
    pulling the catheter partially out of the first segment such that the scaffold moves from the second segment to the first segment, said pulling is performed at a time between said opening the sterilized package and said causing the scaffold to bend, and
    wherein said causing the scaffold to bend includes pushing the catheter into the first segment such that the scaffold moves through the at least one turn of the passageway within the conditioning tube.

7. The method of claim 6, further comprising withdrawing the scaffold out of the passageway of the conditioning tube after said moving the scaffold through the passageway.

8. The method of claim 6, wherein when opening the sterilized packaged, the conditioning tube has already been attached to a region of the carrier tube, and the conditioning tube remains attached to said region of the carrier tube during said pulling the catheter partially out the first segment of the carrier tube and during said pushing the catheter into the first segment of the carrier tube.

9. The method of claim 6, further comprising attaching the conditioning tube to the carrier tube, said attaching performed at a time between said pulling the catheter partially out the first segment of the carrier tube and said pushing the catheter into the first segment of the carrier tube.

10. The method of claim 6, wherein said attaching of the conditioning tube to the carrier tube is performed by replacing the second segment of the carrier tube with the conditioning tube such that the first segment of the carrier tube becomes attached to the conditioning tube.

11. The method of claim 6, wherein the carrier tube is a coiled tube having an arc degree of at least 360 degrees.

\* \* \* \* \*